(12) United States Patent
Levitt

(10) Patent No.: US 6,289,893 B1
(45) Date of Patent: Sep. 18, 2001

(54) SNORE REDUCER JACKET

(76) Inventor: Harold O. Levitt, 128 N. Craig St., Apt. 710, Pittsburgh, PA (US) 15213-2741

( * ) Notice: Subject to any disclaimer, the term of this patent is extended or adjusted under 35 U.S.C. 154(b) by 0 days.

(21) Appl. No.: 09/627,895

(22) Filed: Jul. 27, 2000

Related U.S. Application Data

(60) Provisional application No. 60/147,361, filed on Aug. 6, 1999.

(51) Int. Cl.$^7$ ............................................ A61F 5/56
(52) U.S. Cl. ............................ 128/848; 128/871; 602/902
(58) Field of Search ........................ 128/846, 848, 128/869, 874, 875, 871; 602/902

(56) References Cited

U.S. PATENT DOCUMENTS

| | | | |
|---|---|---|---|
| 132,500 | 10/1872 | Sullivan | 128/871 |
| 663,825 | 12/1900 | Wilson | 128/871 |
| 876,491 | 1/1908 | Rohwer | 128/848 |
| 898,379 | 9/1908 | Liebhardt | 128/848 |
| 2,304,235 | 12/1942 | Boots | 128/871 |
| 3,485,241 | 12/1969 | Polley | 128/871 |
| 4,958,644 | 9/1990 | Rodgers | 128/871 |
| 5,036,865 | 8/1991 | Keaton | 128/848 |
| 5,357,981 | 10/1994 | Eilam et al. | 128/848 |
| 5,381,801 | 1/1995 | McShane et al. | 128/848 |
| 5,383,475 | 1/1995 | Austin | 128/848 |

FOREIGN PATENT DOCUMENTS

| | | | |
|---|---|---|---|
| Nr-162244 | 2/1949 | (DE) | 128/871 |
| 7033 | of 1905 | (GB) | 128/871 |

Primary Examiner—Michael A. Brown

(57) ABSTRACT

The present appliance functions to resist rolling of a sleeping person from a side to a back-reclining position. It thus prevents airway blockage caused by collapsing of soft throat tissues and the back of the tongue due to gravity. The appliance includes a harness having straps encircling the shoulders and chest from a site proximate the mid-thoracic back region of a person, an elongated pouch supported by the harness and extending to opposite lateral sides of the mid-thoracic back region of the person, compressible columns enclosed within said pouch at opposite lateral sides to extend generally vertically and in a general parallel relation spaced apart by a compressible block, each compressible column facing one of the opposite lateral sides of the person, and a ribbed panel overlying the compressible columns and block of sufficient stiffness to maintain gaps between the compressible columns and the person's body until the person attempts to roll from a side-reclining position toward a back-reclining position, in which case one of the gaps closes, allowing compression of one of the columns between the body, the ribbed panel and the bed surface, causing sufficient discomfort to compel the person to return to a side-reclining position.

4 Claims, 2 Drawing Sheets

SNORE REDUCER JACKET

This patent application is a modified and simplified version of provisional application No. 60/147,361 filed Aug. 6, 1999 entitled SNORE HALTER.

BACKGROUND OF THE INVENTION

1. Field of Endeavor

This invention relates principally to mechanical sleep aids, specifically to a lightweight pouch secured to the body to alleviate snoring caused by poor breathing due to airway blockage. It acts to prevent sleeping on one's back where the worst snoring occurs due to soft tissues in the throat collapsing and blocking the airway. When one attempts to roll from a side to a back-reclining position while asleep, the device effectively resists the attempt thus avoiding airway blockage.

Those who snore loudly enough to annoy a sleeping partner or who use oral prostheses for correcting sleep apnea or who are unable to tolerate a Continuous Positive air pressure (C-Pap) breathing apparatus need a device that stays in position on the body and acts effectively when one attempts to roll toward a back-reclining position.

2. Description of Prior Art

Sleep clinics recommend an altered T-shirt to prevent sleeping on one's back and consequent airway blockage. It is to be worn overnight by sleep apnea patients. It has a vertical rear pocket encasing several tennis balls.

This and similar devices often do not achieve the desired objective. The T-shirt doesn't fit snugly enough to prevent the tennis balls from shifting out of position. A more serious disadvantage is that the tennis balls are not compressed until a back-reclining position is reached. Also, it may not provide sufficient resistance to discourage a sound sleeper from remaining on his/her back. There is then no assurance that one will fully reverse the rolling action.

SUMMARY OF THE INVENTION

My invention is fundamentally dissimilar to the tennis ball T-shirt and like devices. With the foregoing in mind, it is an object of the present invention to provide a device that will resist at the outset any rolling action toward one's back and thus prevent airway blockage due to collapsing throat tissues.

The present invention consists of an adjustable, non-slip jacket which is secured to the body at the mid-thoracic region. It is comfortable when one rests on one's side, but provides effective resistance as soon as one attempts to roll from a side to a back-supported position. By training one to remain on one's side, it reduces or even prevents snoring and/or sleep apnea symptoms. It also alerts those whose sleep quality does not improve to consider clinical testing for sleep apnea.

A further object of the invention is to provide a comfortable means of assuring side position reclining while deterring back position reclining. This is accomplished by maintaining gaps between compressible columns located at opposite lateral sides of the device and the body. Rolling toward one's back closes the gap at one of the lateral sides thereby causing one of the compressible columns to impinge upon the body and compel a return to a side position.

DESCRIPTION OF THE DRAWINGS

These features and advantages will be better understood when read in light of the accompanying drawings, in which.

DETAILED DESCRIPTION OF THE INVENTION

Figure 1:
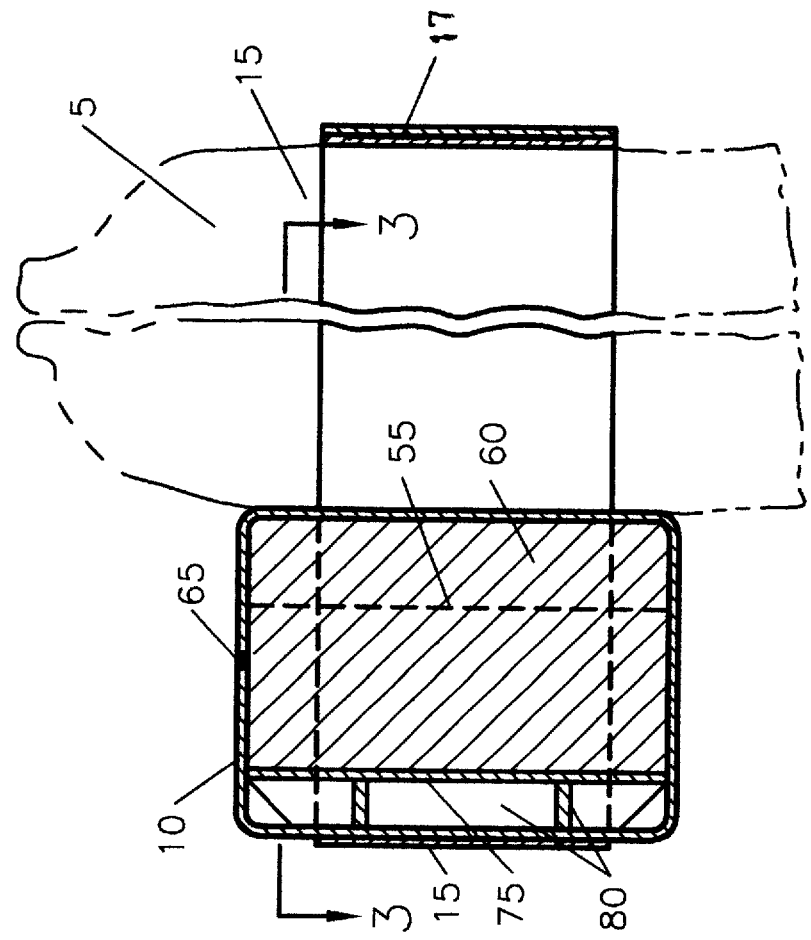
FIG. 1 is a rear elevation view of a person wearing the device according to the present invention.
Figure 2:
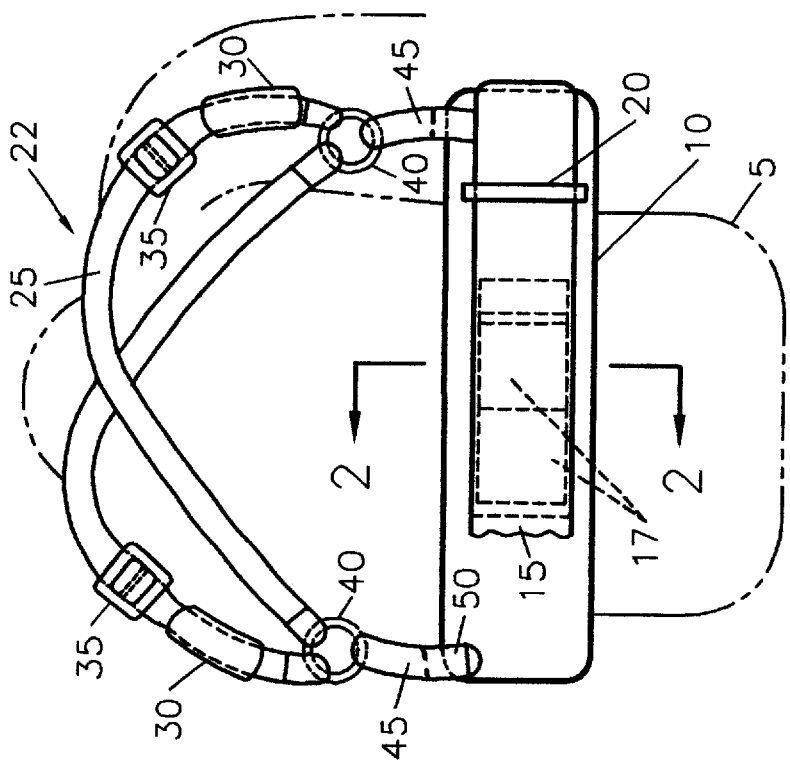
FIG. 2 is an enlarged vertical sectional view taken at cutting plane 2—2 of FIG. 1.
Figure 4:
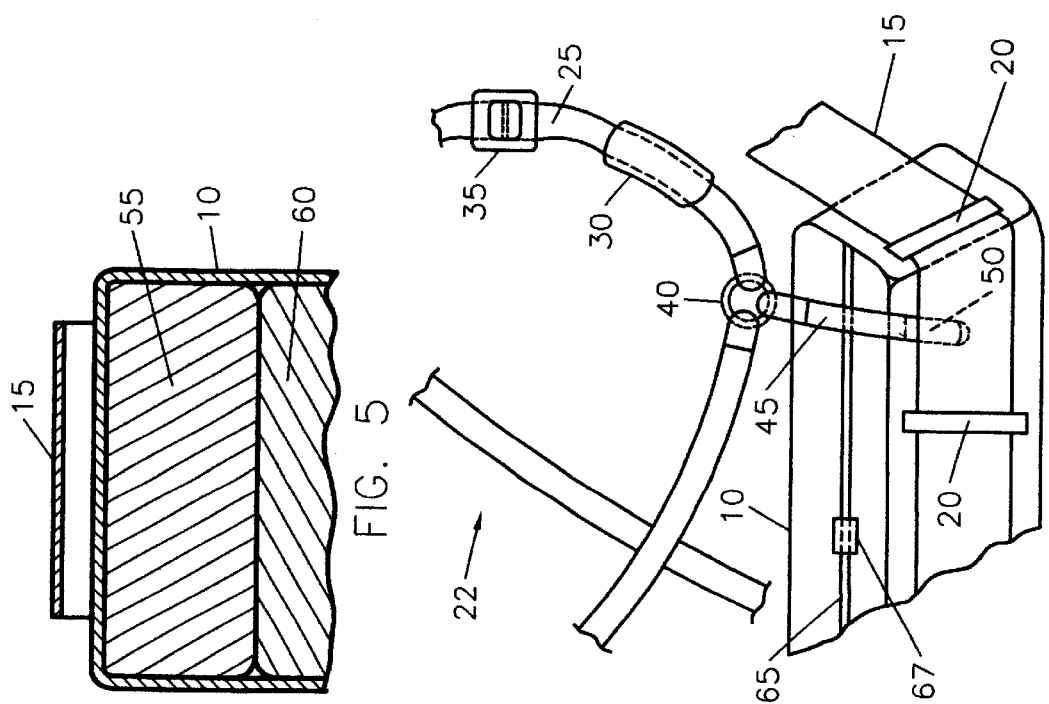
FIG. 4 is a partial elevation view taken at viewing plane 4—4 of FIG. 3B.

Referring to FIGS. 1 and 2, the present device consists of a closed elongated pouch 10 which is secured to one's body 5 by a detachable, elastic belt 15 passing through loops 20 attached to pouch 10. The front ends of belt 15 are joined preferably by velcro strips 17. Referring to FIGS. 2 and 4, a lateral opening 65 across the top of pouch 10 is closed, preferably by a zipper 67, after the internal elements have been installed in the pouch.

Referring to FIGS. 1 and 4, a harness 22 consisting of a pair of cross-connected elastic shoulder straps 25 with cushioning sleeves 30 and length adjustment buckles 35 is connected to a pair of preferably metal rings 40 secured to pouch 10 by loops 45. The loops are attached to opposite lateral sides of pouch 10. They pass through rings 40 and are connected to the pouch at their free ends preferably by velcro strips 50.

Referring to FIGS. 2, 3A, 3B and 5, compressible vertical columns 55 preferably of resilient high density material, for example, 1.7 grade of polyethylene foam, are located inside pouch 10 spaced apart by a compressible elongated rectangular block or separator 60 of resilient low density material, for example, grade 2845 polyurethane foam. A panel 75 of flexible solid material, for example, polyethylene plastic, backed by one or more integral stiffener ribs 80 extends laterally across the rear inside wall of pouch 10 overlying columns 55 and block 60, serving as a leaf spring to maintain gaps 70 between columns 55 and the body 10.

Figure 3A:
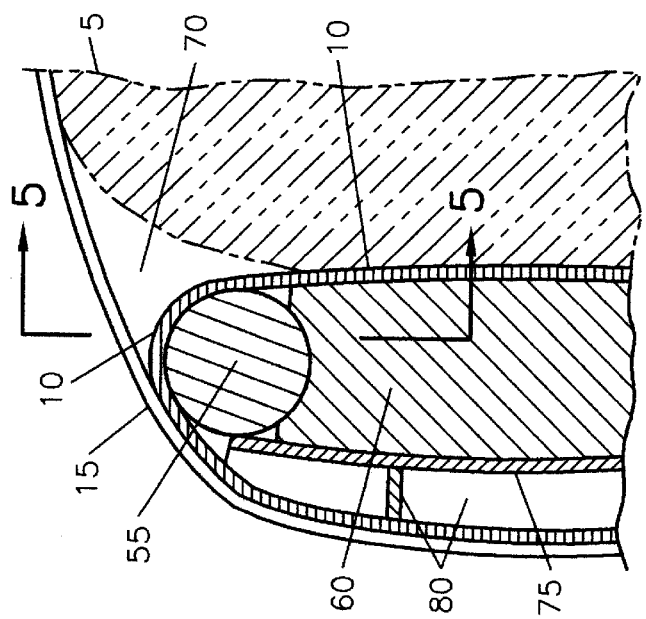
FIGS. 3A and 3B are partial horizontal sectional views of the person and device taken at cutting plane 3—3 of FIG. 2.
Figure 3B:
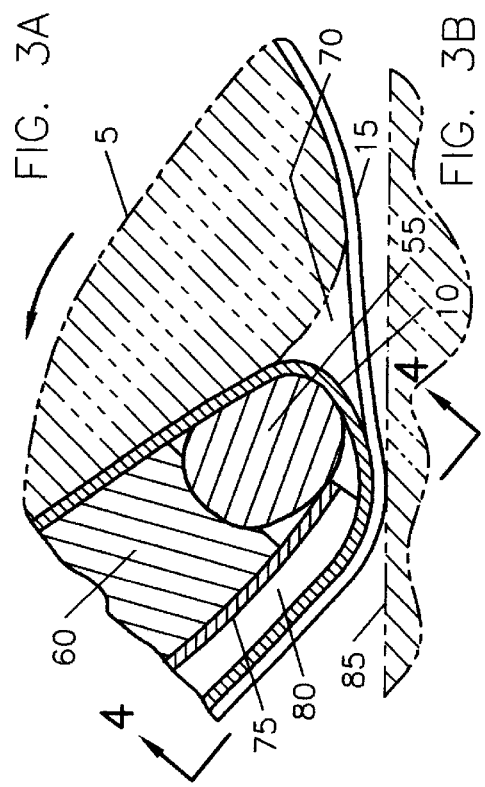
Figure 5:
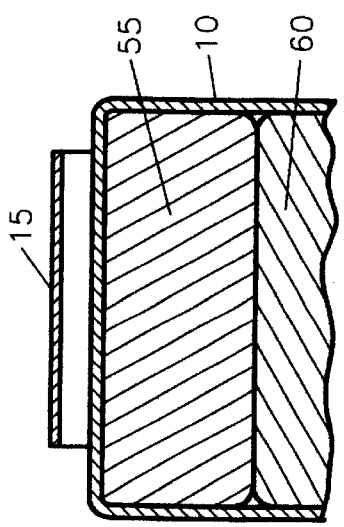
FIG. 5 is a sectional view taken at cutting plane 5—5 of FIG. 3A.

In FIG. 3A, pouch 10 is shown compressed comfortably against the body 5 which is resting on its side. Gaps 70 exist between pouch 10 and the body in the regions of column 55. In FIG. 3B, gap 70 on one lateral side of the pouch has closed due to rolling of the body (in the direction of the arrow) toward a back-reclining position. This causes panel 75 to deflect, squeezing the near column 55 increasingly between the body 5, panel 75 and the bed surface 85 and creating sufficient pressure on the body to compel it to return to the side-reclining position.

It will be appreciated that, in the preferred embodiment, it is desired that the construction and/or material of the low density block 60 are such that its compressibility is substantially greater than that of high density columns 55.

Should one roll completely onto one's back, both ends of panel 75 deflect causing both gaps 70 to close and allowing both columns 55 to bear against the body 5 causing maximum discomfort which compels one to return to a side-reclining position. One is thus trained to remain sleeping on one's side, usually without awakening.

While the present invention has been described in terms of the preferred embodiment, other similar embodiments may be used for performing the same function. Therefore, the present invention should be construed in breadth and scope in accordance with the recitation of the appended claims.

What is claimed is:

1. An appliance to resist rolling of a person's body from a side-reclining to back-reclining position, thus alleviating snoring by preventing closure of the breathing airway, said appliance comprising:

an elongated pouch having an opening extending partially or completely around its periphery;

a belt and belt support loops attached to said pouch and fastening means for joining the belt ends at the front and/or back portion of said pouch;

a harness attached to laterally opposite ends of said pouch and including members encircling the shoulders and chest from a site proximate the mid-thoracic region of a person, said harness including a front and back portion;

compressible columns formed of resilient, high density foam material extending generally vertically and in a general parallel and spaced apart relation enclosed within said elongated pouch at the opposite lateral sides in a manner to locate the columns at the mid-thoracic back region of a person;

a compressible, elongated rectangular block of resilient, low density foam material placed inside said pouch arranged to maintain the spaced apart relation of said compressible columns while maintaining a desired pressure on the central mid-thoracic back region of said person, a ribbed panel of flexible, solid material overlying said compressible columns and said compressible elongated block, the panel being of sufficient stiffness to maintain gaps between the opposite lateral sides of said elongated pouch and the mid-thoracic back region of said person.

2. The appliance according to claim 1 wherein the construction and/or material of said compressible columns are such as to provide effective resistance when one attempts to roll from a side to back-reclining position.

3. The appliance according to claim 1 wherein the construction and/or material of said elongated block are such that the compressibility of the block is substantial, so as to maintain a comfortable relationship between said block and said person in said side-reclining position.

4. The appliance according to claim 1 wherein said panel is characterized by having at least one portion of stiffening ribs along its length to an extent as to hold the compressible columns away from the body of said person but to permit the panel to deflect and cause said compressible columns to provide adequate resistance if the person attempts to roll toward a back-reclining position.

* * * * *